(12) United States Patent
Ooi (10) Patent No.: US 7,067,814 B2
(45) Date of Patent: Jun. 27, 2006

(54) RADIATION DETECTOR AND A METHOD OF MANUFACTURING THE DETECTOR

(75) Inventor: Junichi Ooi, Kyoto-fu (JP)

(73) Assignee: Shimadzu Corporation, Kyoto-fu (JP)

( * ) Notice: Subject to any disclaimer, the term of this patent is extended or adjusted under 35 U.S.C. 154(b) by 249 days.

(21) Appl. No.: 10/847,393

(22) Filed: May 18, 2004

(65) Prior Publication Data

US 2004/0262527 A1    Dec. 30, 2004

(30) Foreign Application Priority Data

Jun. 30, 2003  (JP)  ............................. 2003-187890
Mar. 22, 2004  (JP)  ............................. 2004-082407

(51) Int. Cl.
*G01T 1/20* (2006.01)
(52) U.S. Cl. .................................................. 250/368
(58) Field of Classification Search ................ 250/368
See application file for complete search history.

(56) References Cited

U.S. PATENT DOCUMENTS 4,750,972 A * 6/1988 Casey et al. .................. 216/24
5,329,124 A * 7/1994 Yamamoto et al. ......... 250/367

FOREIGN PATENT DOCUMENTS

JP           06-095146 A1    11/1994

* cited by examiner

*Primary Examiner*—David Porta
*Assistant Examiner*—Mindy Vu
(74) *Attorney, Agent, or Firm*—Rader, Fishman & Grauer PLLC (57) ABSTRACT

A radiation detector has a lattice frame laid in a light guide. The lattice frame is prepared by combining thin strips of optical elements, i.e. light reflecting elements. In manufacture, the lattice frame is placed in a recess of a trestle, and a thoroughly defoamed, optically transparent liquid resin is poured into the recess. After the liquid resin cures, the lattice frame and the resin form the light guide which is then removed from the trestle. The light guide is then contoured by cutting and polishing. This construction allows a thickness and angles of the light reflecting elements freely, and has no gaps formed between the reflecting elements and transparent resin, thereby assuring high reflecting efficiency.

20 Claims, 8 Drawing Sheets

RADIATION DETECTOR AND A METHOD OF MANUFACTURING THE DETECTOR

BACKGROUND OF THE INVENTION (1) Field of the Invention

This invention relates to a radiation detector having scintillators, a light guide and photomultiplier tubes arranged in the stated order and optically combined to one another, and to a method of manufacturing the radiation detector.

(2) Description of the Related Art

This type of radiation detector is used in a medical diagnostic apparatus such a PET (Positron Emission Tomography) apparatus or a SPECT (Single Photon Emission Computed Tomography) apparatus for detecting radiation (e.g. gamma rays) released from radioisotopes (RI) introduced into a patient and accumulated in a site of interest, and obtaining sectional images of RI distribution in the site of interest. The radiation detector includes scintillators that emit light in response to incident gamma rays released from the patient, and photomultiplier tubes for converting the light emitted from the scintillators to pulsed electric signals. An earlier radiation detector had the scintillators and photomultiplier tubes arranged in a one-to-one relationship. In recent years, a technique has been employed to combine a plurality of scintillators to photomultiplier tubes smaller in number than the scintillators. With this technique, positions of incidence of gamma rays are determined from power ratios of the photomultiplier tubes to enhance resolution. A construction of a conventional radiation detector will be described hereinafter with reference to the drawings.

Figure 1:
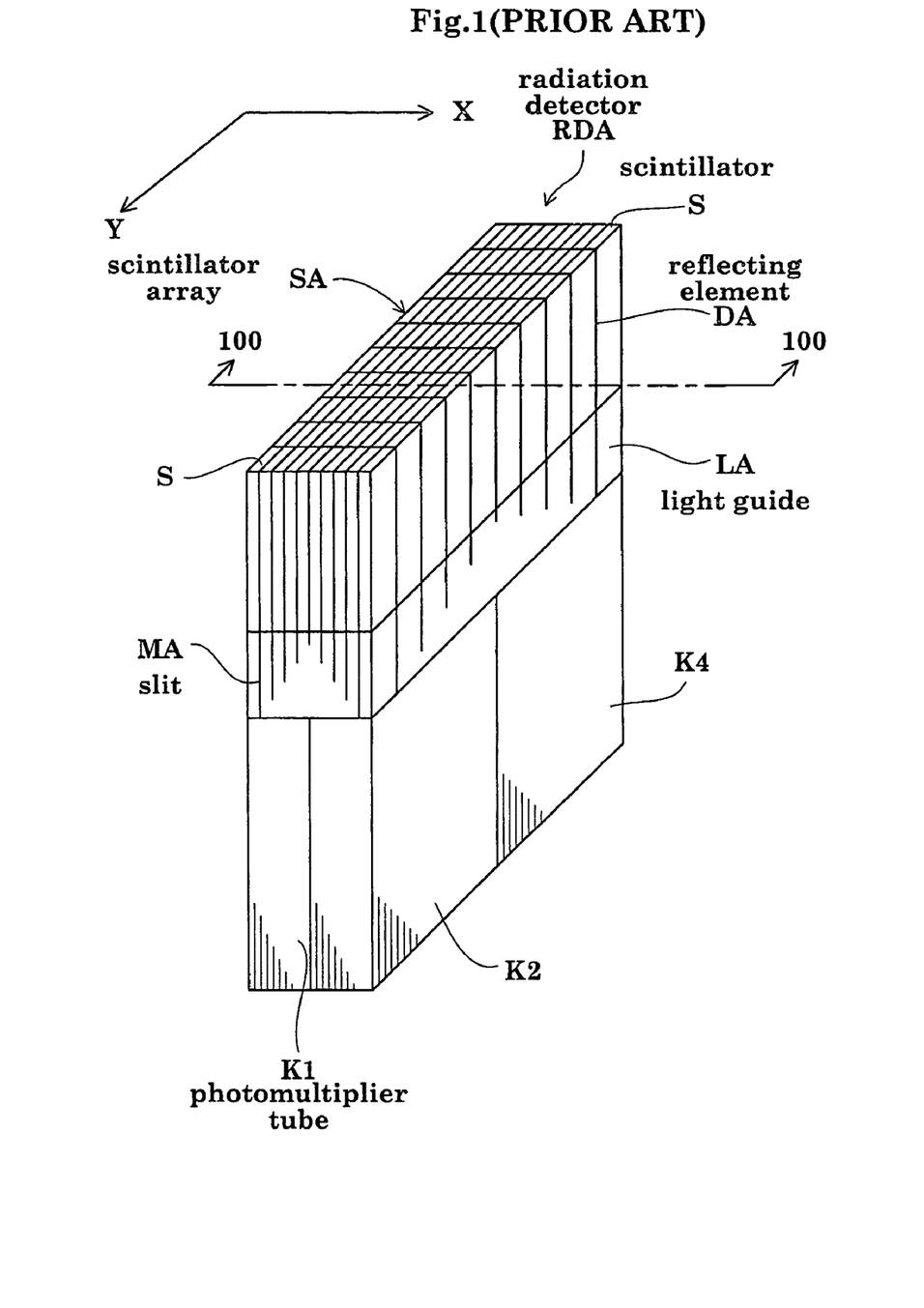
FIG. 1 is a view showing an outward appearance of a conventional radiation detector.
Figure 2:
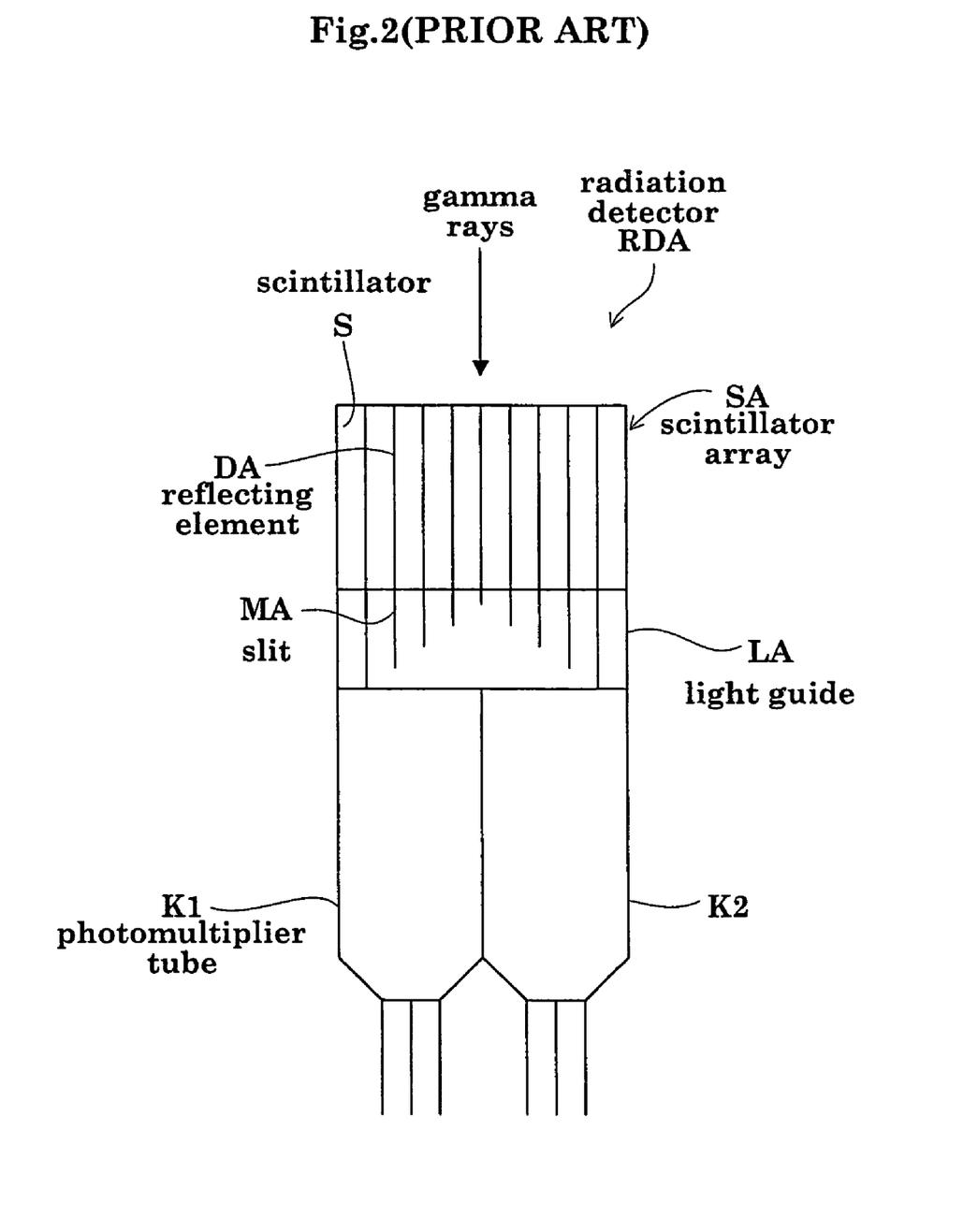
FIG. 2 is a section of the conventional radiation detector taken on line 100—100 of FIG. 1.

FIG. 1 is a schematic view showing an outward appearance of a conventional radiation detector. FIG. 2 is a section taken on line 100—100 of FIG. 1. FIGS. 1 and 2 show an example disclosed in Japanese Patent Publication No. 06-95146 (1994). This radiation detector RDA includes a scintillator array SA, a light guide LA optically combined to the scintillator array SA, a plurality of (four in FIGS. 1 and 2) photomultiplier tubes K1, K2, K3 (not seen in the figures) and K4 optically combined to the light guide LA. The scintillator array SA is an aggregate of scintillators S divided by numerous light reflecting elements DA inserted peripherally thereof. The scintillator array SA may be surrounded by light reflectors (not shown).

With this radiation detector RDA, the light guide LA is formed of an optically transparent material defining numerous slits MA of predetermined depths cut by a dicing saw or wire saw. The slits MA have optical elements (e.g. light reflecting elements or light transmitting elements) inserted therein. The slits MA have larger lengths from inner to outer positions of the light guide LA. This construction adjusts quantities of light from the scintillators S distributed to the four photomultiplier tubes K1–K4 to discriminate positions of incidence of gamma rays.

The conventional radiation detector RDA noted above has the following drawbacks.

The radiation detector RDA is a high-resolution detector using the scintillators S of high sensitivity as proposed in recent years, and the scintillator array SA has far more scintillators than the scintillator array of an earlier detector. Consequently, each scintillator S has a smaller section than a scintillator in the earlier detector. Generally, the smaller scintillators S provide, by absorption or diffusion, the lower probability of photons produced inside moving into the light guide LA. This reduces the capability of discriminating, and thus detecting, positions of incidence of gamma rays.

Further, because of limitations imposed by the shape of photomultiplier tubes K1–K4 and the shape of scintillators S, the X-direction (see FIG. 1) and Y-direction (see FIG. 1) are not necessarily in optically the same spatial relationship. It is therefore difficult to select widths of the light guide LA. Specifically, in the conventional example using two sets of 2-channel built-in photomultiplier tubes of 1-inch square, i.e. the four photomultiplier tubes K1–K4, the light guide LA must have a thickness of at least 10 mm in order to divide a 50 mm into ten in the Y-direction, and a thickness not exceeding 4 mm to divide a 25 mm into nine in the X-direction. That is, in order to distribute light emitted from the scintillators S to the photomultiplier tubes K1–K4 through the light guide LA, the light guide LA must have a thickness corresponding to the scintillators S or widths in the X- and Y-directions of the light guide LA. Thus, a reduction in size of each scintillator S causes a conflict between required specifications in the X- and Y-directions of the thickness of the light guide LA.

From the manufacturing point of view, a high accuracy of finishing is required particularly for the light guide LA optically combined to the scintillator array SA in order not to lower light transmission efficiency, and at the same time it is necessary to make the width of slits MA as small as possible. However, the accuracy of finishing the light guide LA is low where, as in the above conventional example, the radiation detector RDA is manufactured by cutting an optically transparent material with a dicing saw or wire saw to form the slits MA. Furthermore, the slits MA inevitably have coarse surfaces and have large widths. The light guide LA in the conventional example is manufactured by cutting the material into a plurality of parts with the dicing saw or wire saw to form the slits MA, and then combining the parts. This assembling operation is complicated and results in a cost increase.

When suitable light reflecting elements DA are inserted in the slits MA after the above process, gaps are formed between the reflecting elements DA and slits MA, thereby lowering reflection efficiency also. As these factors reduce output by incident gamma rays to make an accurate discrimination of positions impossible, an overall image quality will also deteriorate.

More particularly, a reduced discriminating ability results in a reduction in resolution. Where such radiation detector RDA is used in a medical diagnostic apparatus such as a PET apparatus or SPECT apparatus, images obtained by the apparatus will have poor quality. When a site of interest is a tumor, for example, the tumor may not be accurately outputted on the image.

Further, with the conventional processing method, it is difficult to form slits MA inclined relative to the direction of arrangement of the scintillator array SA.

SUMMARY OF THE INVENTION

This invention has been made having regard to the state of the art noted above, and its object is to provide a radiation detector and a method of manufacturing the radiation detector, capable of maintaining high image quality with high resolution, which may be realized simply.

To fulfill the above object, Inventors have made intensive research and attained the following findings.

From the manufacturing point of view, the following approach is conceivable in order to realize a radiation detector simply. Cubicles are formed in a lattice frame which is a combination of plate-like optical elements, typically light reflecting elements or light transmitting elements. A transparent liquid resin is poured into a rectangular vessel which can hold this lattice frame. The resin is allowed to cure with the above lattice frame placed in the vessel. The cured resin integrating the liquid resin and lattice frame is taken out of the rectangular vessel, and is put into shape as a light guide. This manufacturing process can avoid the complication of assembly and lowering of the ability to discriminate positions of incidence of gamma rays.

Further, a contrivance based the following new finding has proved effective to improve the ability to discriminate positions of incidence and thus to improve image quality. Where, for example, a discrepancy occurs between the shape of a plane of incidence of the photomultiplier tubes of light from the light guide and the shape of a plane of the scintillator array opposed to the photomultiplier tubes, the light guide interposed between the photomultiplier tubes and the scintillator array must have a complicated shape matching the above discrepant shapes.

Figure 9A:
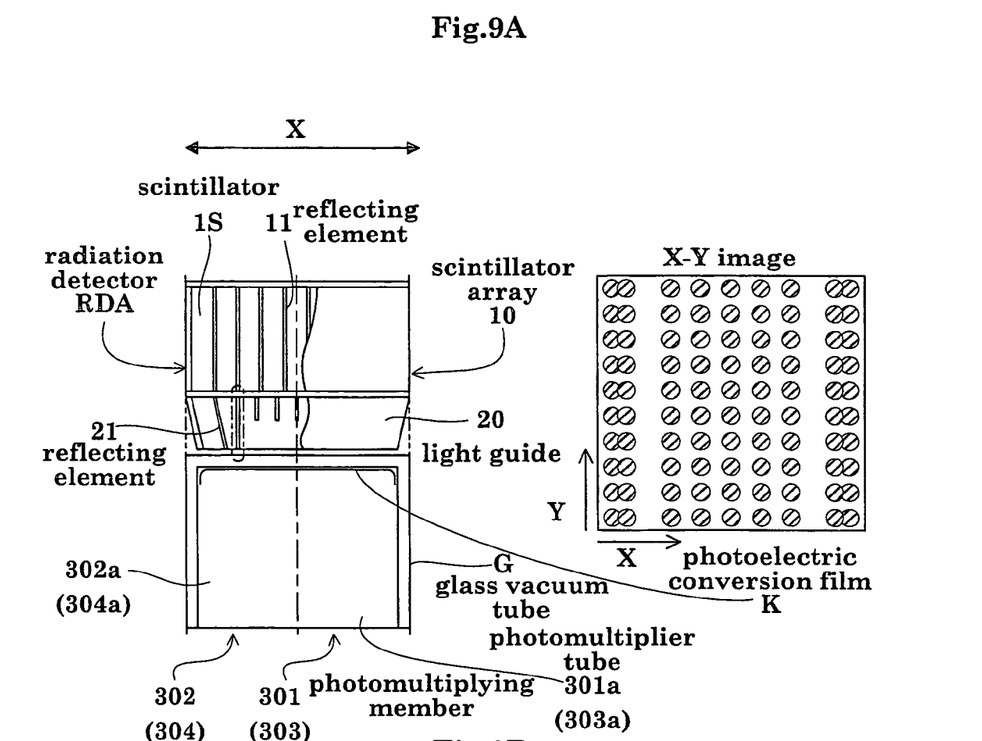
FIG. 9A is a view showing an outward appearance in the X-direction seen from the Y-direction, and results of detection for the X- and Y-directions.
Figure 9B:
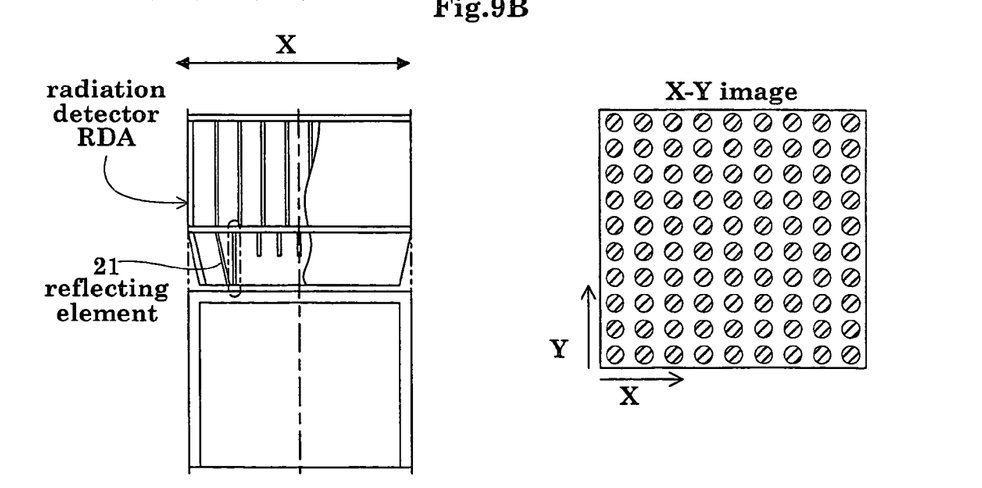
FIG. 9B is a view showing an outward appearance in the X-direction seen from the Y-direction, and results of detection for the X- and Y-directions.

In such a case, as shown in FIG. 9A, light reflecting elements 21 are arranged equidistantly (i.e. uniformly) in a direction of arrangement of scintillators 10, in a light guide 20 except in peripheral regions thereof. Conversely, as shown in FIG. 9B, the second reflecting element 21 from the left end (portion enclosed by an alternate long and short dash line in FIGS. 9A and 9B) is slightly shifted, so that an interval between this second reflecting element 21 and the next reflecting element 21 to the right is different from intervals between the other reflecting elements 21 arranged rightward. Then, the structure shown in FIG. 9B is an improvement upon the structure shown in FIG. 9A in discriminating positions of incidence of gamma rays and detecting the gamma rays.

Thus, the light reflecting elements heretofore arranged at equidistantly in the direction of arrangement of the scintillators may be adjusted, for example, to have different intervals therebetween in response to results of discrimination of positions of incidence and detection of gamma rays. It has been found that such adjustment of the arrangement improves the abilities to discriminate positions of incidence of gamma rays and detect the gamma rays.

Similarly, the light reflecting elements heretofore oriented perpendicular to the direction of arrangement of the scintillators may be adjusted to have an angle thereto, e.g. to be oblique, in response to the results noted above. Such adjustment also has been found to improve the abilities to discriminate positions of incidence of gamma rays and detect the gamma rays. Further, the light reflecting elements heretofore arranged at intervals corresponding to the intervals of the scintillators may be adjusted to have different intervals to those of the scintillators in response to the results noted above. Such adjustment also has been found to improve the abilities to discriminate positions of incidence of gamma rays and detect the gamma rays. The above adjustments have been found effective not only for the light reflecting elements but also for optical elements, typically light transmitting elements, for example, in improving the above-noted abilities. Thus, it has been found that high image quality with high resolution may be maintained by effecting the various adjustments of the light guide.

Based on the above findings, this invention provides a radiation detector having a scintillator array formed of a plurality of scintillators in a compact, two-dimensional arrangement, a light guide optically combined to the scintillator array, and a plurality of photomultiplier tubes smaller in number than the scintillators and optically combined to the light guide, wherein:

the light guide is formed of at least a lattice frame having plate-like optical elements combined crosswise, and a transparent liquid resin, the lattice frame defining a plurality of cubicles; and the optical elements forming the cubicles are subjected to at least one of (a) an adjustment to predetermined intervals in a direction of arrangement of the scintillator array, (b) an adjustment to a predetermined angle to the direction of arrangement of the scintillator array, and (c) an adjustment to intervals different from intervals between the scintillators.

With the radiation detector according to this invention, when radiation impinges on one scintillator in the scintillator array having a plurality of scintillators in a compact, two-dimensional arrangement, that scintillator will absorb the radiation and emit light. Part of this light is transmitted through adjacent scintillators, but a major part of the light enters the light guide while repeating passage and dispersion due to reflections inside the scintillator. The light incident on the light guide is dispersed by cubicles defined by the optical elements forming the light guide, and enters the photomultiplier tubes.

In order that the quantity of light incident on the photomultiplier tubes may vary equally according to the positions of the scintillators on which radiation impinges, the optical elements are subjected to at least one of (a) an adjustment to predetermined intervals in a direction of arrangement of the scintillator array, (b) an adjustment to a predetermined angle to the direction of arrangement of the scintillator array, and (c) an adjustment to intervals different from intervals between the scintillators. Such adjustment improves the discriminating ability to maintain high resolution and high image quality.

In another aspect of the invention, there is provided a method of manufacturing a radiation detector having a scintillator array formed of a plurality of scintillators in a compact, two-dimensional arrangement, a light guide optically combined to the scintillator array, and a plurality of photomultiplier tubes smaller in number than the scintillators and optically combined to the light guide. This method comprises:

(A) a step of fabricating a lattice frame by combining a plurality of plate-like optical elements crosswise;

(B) a step of pouring a transparent liquid resin into a rectangular vessel for receiving the lattice frame, before or after placing the lattice frame in the rectangular vessel; and (C) a step of removing from the rectangular vessel a cured resin object integrating the liquid resin having cured and the lattice frame, and contouring the resin object to make the light guide;

wherein the step (A) above is executed to combine the optical elements by making at least one of (a) an adjustment to predetermined intervals in a direction of arrangement of the scintillator array, (b) an adjustment to a predetermined angle to the direction of arrangement of the scintillator array, and (c) an adjustment to intervals different from intervals between the scintillators.

With the method of manufacturing a radiation detector according to this invention, the optical elements may be arranged in the light guide through the steps (A) to (C), without being cut with a dicing saw or wire saw. This realizes a radiation detector with high finishing accuracy. The radiation detector is manufactured simply through the steps (A) to (C).

In the above radiation detector and manufacturing method, the light guide may be formed by making at least one of adjustments (a) to (c). Thus, the light guide may be formed by making only adjustment (a), (b) or (c), or a combination of two adjustments (a) and (b), (b) and (c) or (c) and (a), or a combination of all three adjustment (a) to (c).

As a specific example of adjustment (a), the optical elements may be arranged at unequal intervals. As a specific example of adjustment (b), the optical elements may be inclined at an oblique angle to the direction of arrangement of the scintillator array.

In a preferred example of the above radiation detector and manufacturing method according to this invention, the light guide is constructed such that a perimeter of a plane of the scintillator array opposed to the light guide matches a perimeter of a plane of the light guide opposed to the scintillator array. With this construction, the light from the scintillators may impinge on the light guide without escaping outside the light guide.

In another preferred example of the above radiation detector and manufacturing method according to this invention, each of the photomultiplier tubes includes a vacuum tube, and a photomultiplying member contained in the vacuum tube, the light guide being constructed such that a perimeter of a plane of the light guide opposed to the photomultiplier tubes matches a perimeter of a plane of the photomultiplying members opposed to the light guide. With this construction, the light from the light guide may impinge on the photomultiplying members without escaping outside the photomultiplying members.

In a further preferred example of the above radiation detector and manufacturing method according to this invention, each of the photomultiplier tubes includes a vacuum tube, and a photomultiplying member contained in the vacuum tube, the light guide having outer peripheries thereof inclined such that such that a perimeter of a plane of the scintillator array opposed to the light guide matches a perimeter of a plane of the light guide opposed to the scintillator array, and that a perimeter of a plane of the light guide opposed to the photomultiplier tubes matches a perimeter of a plane of the photomultiplying members opposed to the light guide. With this construction, the light from the scintillators may impinge on the light guide without escaping outside the light guide, and the light from the light guide may impinge on the photomultiplying members without escaping outside the photomultiplying members. Those of the optical elements adjoining the outer peripheries may be inclined to match inclinations of the outer peripheries. The light could be trapped in narrow spaces between the outer peripheries and the next optical elements. These optical elements inclined to match inclinations of the outer peripheries effectively avoid such trapping of the light.

In the above radiation detector and manufacturing method according to this invention, the optical elements may be light reflecting elements or light transmitting elements.

In the above manufacturing method according to this invention, the liquid resin, preferably, is an optically transparent epoxy resin or acrylic resin. Preferably, a release agent is applied to the rectangular vessel before executing the step (B) of pouring the transparent liquid resin into the rectangular vessel. Then, when executing the step (C), i.e. removing from the rectangular vessel a cured resin object integrating the liquid resin having cured and the lattice frame, and contouring the resin object to make the light guide, the resin object may be removed from the rectangular vessel easily. Preferably, the liquid resin is defoamed when executing the step (B) of pouring the transparent liquid resin into the rectangular vessel. By defoaming the liquid resin, the cured resin becomes free from voids formed therein, thus avoiding lowering of resolution due to such voids. As a defoaming method, the liquid resin may be poured in after being defoamed, or the liquid resin may be poured in while carrying out vacuum degassing, after placing the rectangular vessel in a space that may be vacuum-degassed.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

A preferred embodiment of this invention will be described in detail hereinafter with reference to the drawings.

Figure 3:
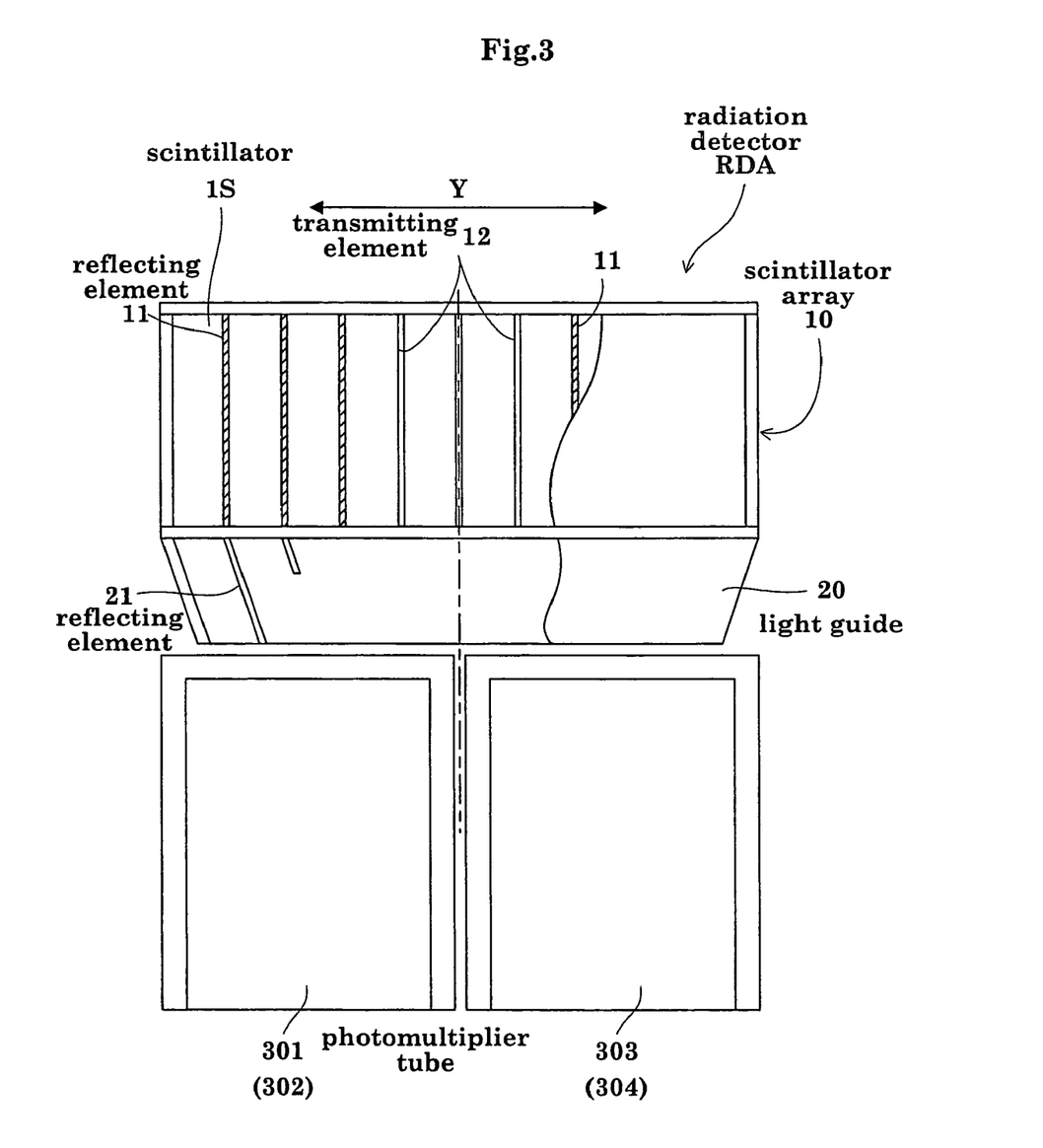
FIG. 3 is a view showing an outward appearance, in a Y-direction seen from an X-direction, of a radiation detector in one embodiment of this invention.
Figure 4:
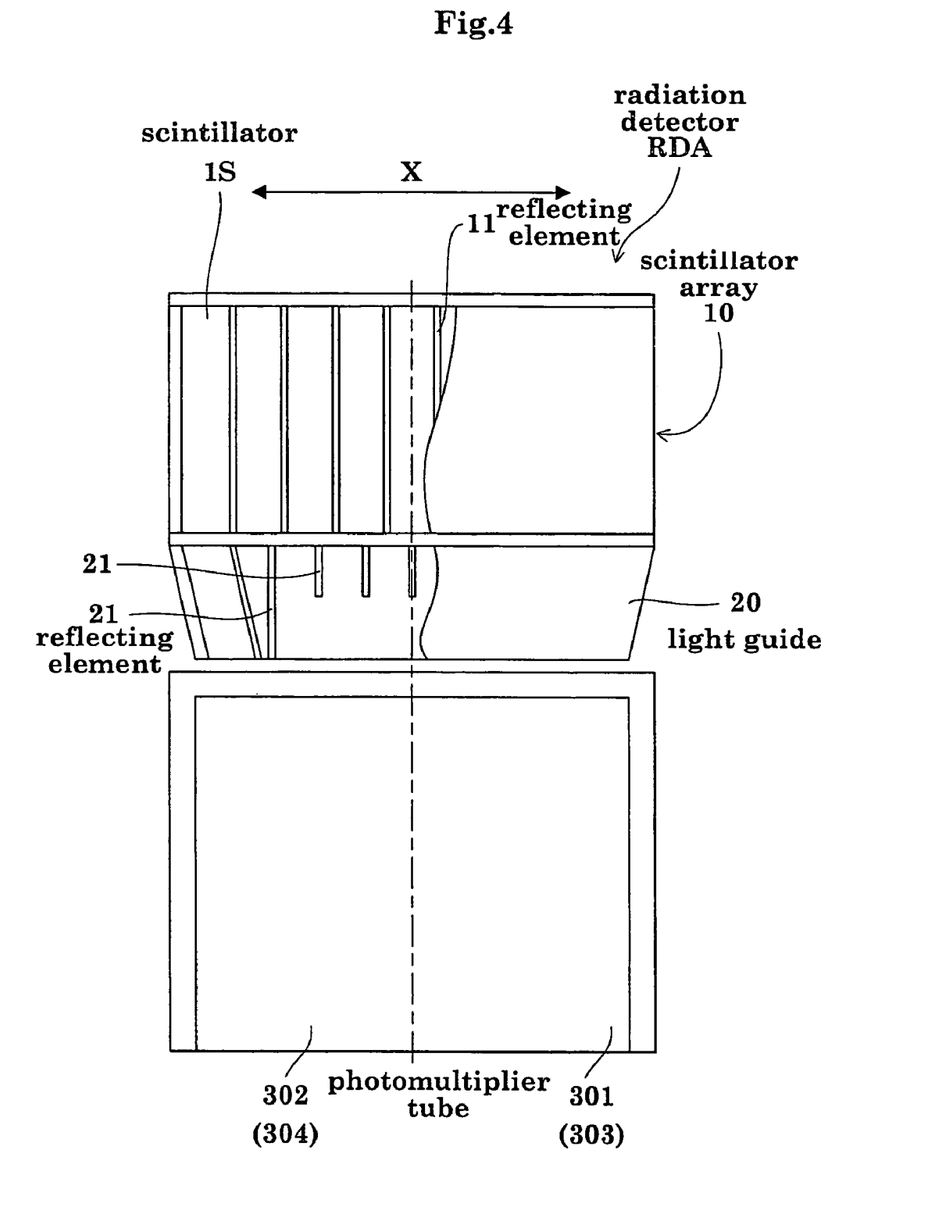
FIG. 4 is a view showing an outward appearance, in the X-direction seen from the Y-direction, of the radiation detector.

FIG. 3 is a view (front view) showing an outward appearance, in a Y-direction seen from an X-direction, of a radiation detector in one embodiment of this invention. FIG. 4 is a view (side view) showing an outward appearance, in the X-direction seen from the Y-direction, of the radiation detector;

The radiation detector RDA in this embodiment includes a scintillator array 10, a light guide 20 optically combined to the scintillator array 10, and four photomultiplier tubes 301, 302, 303 and 304 optically combined to the light guide 20. FIG. 3 shows the photomultiplier tube 301 and photomultiplier tube 303. FIG. 4 shows the photomultiplier tube 301 and photomultiplier tube 302.

Figure 6:
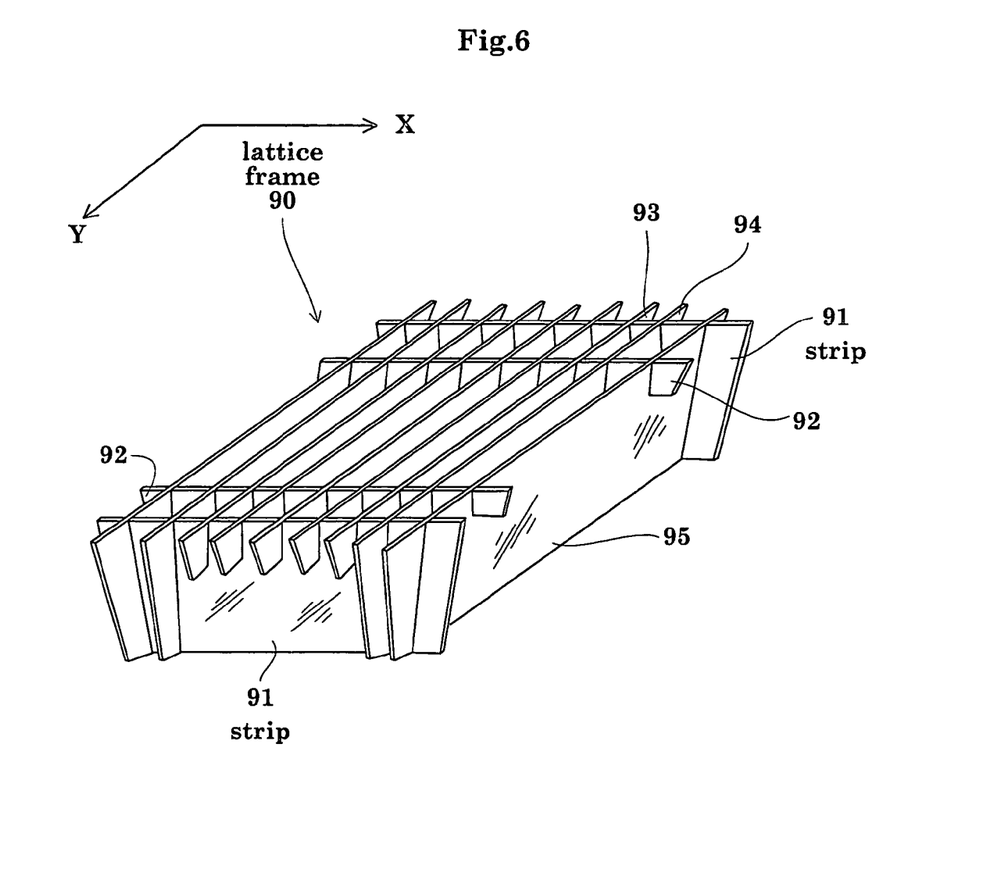
FIG. 6 is a perspective view of a lattice frame of the light guide.

The scintillator array 10 has scintillators 1S in a compact, two-dimensional arrangement, the scintillators 1S being defined by light reflecting elements 11 and light transmitting elements 12. In this embodiment, 90 scintillators 1S in total are arranged two-dimensionally, with nine arranged in the X-direction and ten in the Y-direction. The light guide 20 has a lattice frame 90 with strips 91–95 of optical elements such as light reflecting elements 21 combined crosswise (FIG. 6). This lattice frame 90 defines numerous cubicles. The scintillators 1S are formed of an inorganic crystal such as $Bi_4Ge_3O_{12}$ (BGO), $Gd_2SiO_5$ (GSO), $Lu_2SiO_5$:Ce ($Lu_2SiO_5$ doped with Ce, i.e. LSO), LuYSiO$_5$:Ce (LuYSiO$_5$ doped with Ce, i.e. LYSO), NaI (sodium iodide), $BaF_2$ (barium fluoride) or CsF (cesium fluoride).

In this embodiment, light reflecting elements 11 are interposed between all the scintillators 1S arranged in the X-direction. With the ten scintillators 1S arranged in the Y-direction, light transmitting elements 12 are interposed between the four scintillators 1S in the middle, and light reflecting elements 11 between the other scintillators 1S.

As shown in FIGS. 9A and 9B, each photomulipler tube 301 (302–304) includes a glass vacuum tube G, and a photomultiplying member 301a (302a–304a) contained in the vacuum tube G. Specifically, in this embodiment, the glass vacuum tubes G are formed to have a 1-inch square shape, and a photoelectric conversion film K is disposed in each glass vacuum tube G opposite the light guide 20. This embodiment provides two sets of photomultiplier tubes of 1-inch square shape with two built-in channels. One of the sets has two-channel photomultiplying members 301a and 302a mounted in the glass vacuum tube G of 1-inch square. The other set also has two-channel photomultiplying members 303a and 304a mounted in the glass vacuum tube G of 1-inch square.

A discrepancy occurs between the shape of a plane of incidence (i.e. a perimeter) of photomultipler tubes 301–304 of light from the light guide 20 and the shape of a plane of the scintillator array 10 opposed to the photomultiplier tubes 301–304. As shown in FIGS. 3 and 4, where the plane of incidence of the photomultiplier tubes 301–304 is smaller in area, outer peripheries of the light guide 20 are inclined to match that plane. That is, outer peripheries of the light guide 20 are inclined so that the perimeter of the plane of the light guide 20 opposed to the photomultiplier tubes 301–304 matches the perimeter of the plane of the photomultiplying members 301a–304a opposed to the light guide 20, and that the perimeter of the plane of the scintillator array 10 opposed to the light guide 20 matches the perimeter of the plane of the light guide 20 opposed to the scintillator array 10.

Preferably, outer peripheries of the light guide 20 are inclined so that the perimeter of the plane of the light guide 20 opposed to the photomultiplier tubes 301–304 matches the perimeter of the photoelectric conversion films K of the photomultiplier tubes 301–304.

As shown in FIG. 4, when gamma rays impinge on the nine scintillators 1S arranged in the X-direction, the scintillators 1S absorb the gamma rays and emit light. Specifically, the gamma rays are converted to visible light. This light is led to the photomultiplier tubes 301–304 through the light guide 20 combined optically. The positions, lengths and angles of the respective light reflecting elements 21 in the light guide 20 are adjusted so that the photomultiplier tube 301 (303) and photomultiplier tube 302 (304) arranged in the X-direction have a power ratio varying at a predetermined rate.

More particularly, the lengths of the light reflecting elements 21 and intervals between the reflecting elements 21 are adjusted to predetermined intervals and angles relative to the direction of arrangement of the scintillator array 10 so that a calculation (P1−P2)/(P1+P2), where P1 is the output of photomultiplier tube 301 and P2 is the output of photomultiplier tube 302, changes at a predetermined rate according to the position of each scintillator 1S. The longer reflecting elements 21 result in the higher discriminating ability of the scintillators 1S, but also in the greater attenuation of light. The discriminating ability is improved without reducing the quantity of light only by slightly changing the positions, angles and lengths.

On the other hand, the ten scintillators 1S arranged in the Y-direction, as do the scintillators 1S arranged in the X-direction, emit light which is led to the photomultiplier tubes 301–304 through the light guide 20 optically combined. The positions, lengths and angles of the respective light reflecting elements 21 in the light guide 20 are adjusted so that the photomultiplier tube 301 (302) and photomultiplier tube 303 (304) arranged in the Y-direction have a power ratio varying at a predetermined rate.

This aspect will be described with reference to FIGS. 9A and 9B. FIGS. 9A and 9B are views showing an outward appearance in the X-direction seen from the Y-direction, and results of detection for the X- and Y-directions. The results of detection for the X- and Y-directions ("X-Y images" in FIGS. 9A and 9B) are shown schematically. The hatched portions in FIGS. 9A and 9B show output distributions of the light converted from the gamma rays, i.e. distributions of positions of incidence of the gamma rays on the scintillator array 10. In FIGS. 9A and 9B, outer peripheries of the light guide 20 are inclined, and the light reflecting elements 21 next to the outer peripheries, i.e. the light reflecting elements 21 arranged at the ends, are also inclined to match the inclined outer peripheries. In FIGS. 9A and 9B, adjacent the middle of the light guide 20, the light reflecting elements 21 are arranged equidistantly (i.e. uniformly) in the direction of arrangement of the scintillator array 10. In FIGS. 9A and 9B, the light reflecting elements 21 in a middle region are arranged at intervals different from the intervals between the scintillators 1S. The second light reflecting element 21 from the left end in FIG. 9A (portion enclosed by an alternate long and short dash line in FIGS. 9A and 9B) is slightly shifted so that, as seen in FIG. 9B, an interval between this second reflecting element 21 and the next reflecting element 21 to the right is different from the intervals between the other reflecting elements 21 arranged rightward. It has been confirmed that this adjustment, compared with an unadjusted case, improves the ability to discriminate positions of incidence of gamma rays and to detect the gamma rays. It will be appreciated that the adjustment to make the interval between the second reflecting element 21 and the next reflecting element 21 to the right different from the intervals between the other reflecting elements 21 arranged rightward results in uneven intervals between certain of the light reflecting elements 21.

Peripheral surfaces not opposed to the scintillators 1S, except the plane optically combined to the photomultiplier tubes 301–304, are covered by a light reflecting material (not shown).

Figure 5:
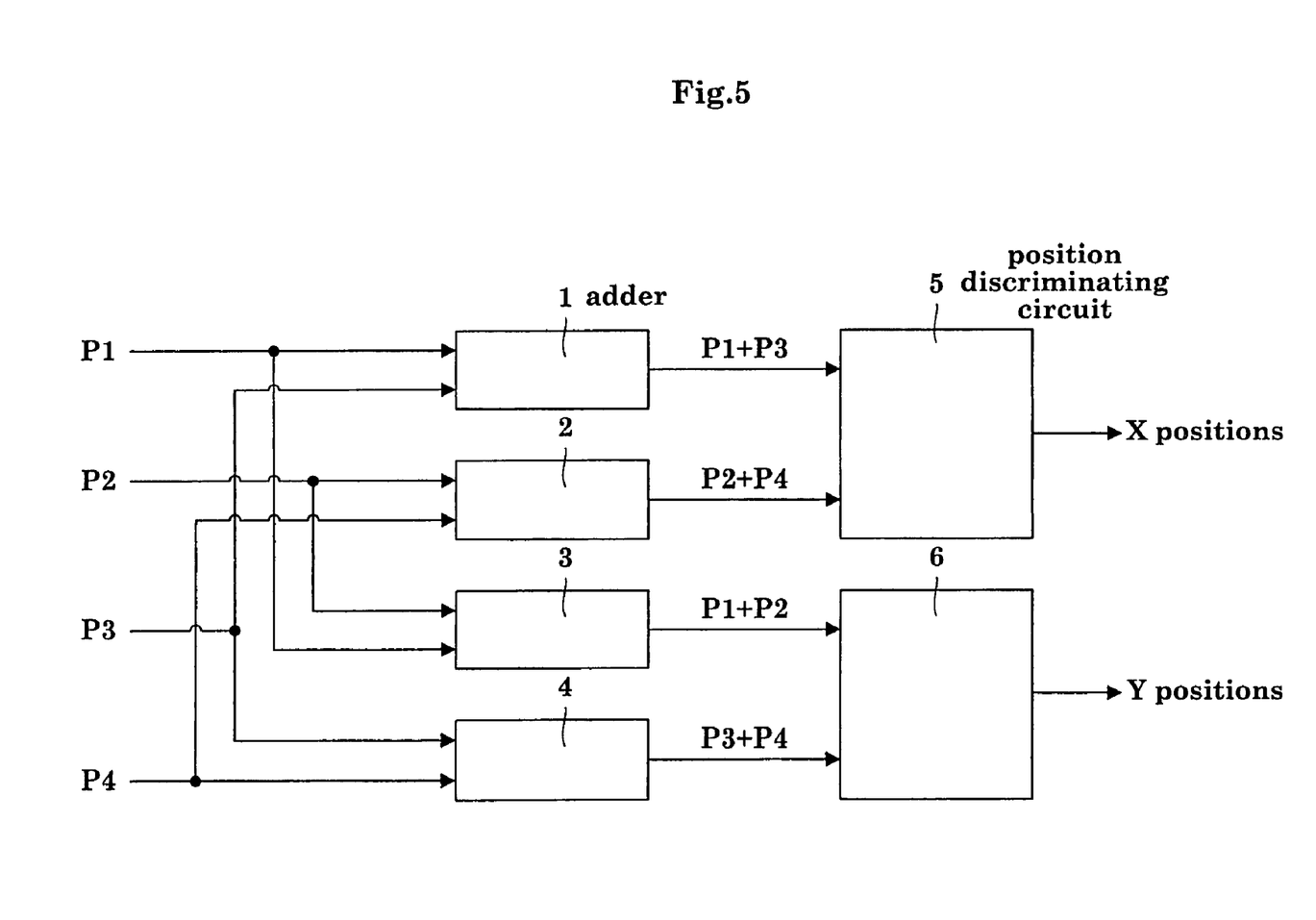
FIG. 5 is a block diagram showing a position calculating circuitry of the radiation detector.

FIG. 5 is a block diagram showing a position calculating circuitry of the radiation detector. The position calculating circuitry includes adders 1, 2, 3 and 4, and position discriminating circuits 5 and 6. Referring to FIG. 5, in order to detect positions of incidence of gamma rays in the X-direction, output P1 of the photomultiplier tube 301 and output P3 of the photomultiplier tube 303 are inputted to the adder 1, and output P2 of the photomultiplier tube 302 and output P4 of the photomultiplier tube 304 are inputted to the adder 2. Added outputs (P1+P3) and (P2+P4) of the two adders 1 and 2 are inputted to the position discriminating circuit 5, and positions of incidence of gamma rays in the X-direction are determined from the two added outputs.

Similarly, in order to detect positions of incidence of gamma rays in the Y-direction, output P1 of the photomultiplier tube 301 and output P2 of the photomultiplier tube 302 are inputted to the adder 3, and output P3 of the photomultiplier tube 303 and output P4 of the photomultiplier tube 304 are inputted to the adder 4. Added outputs (P1+P2) and (P3+P4) of the two adders 3 and 4 are inputted to the position discriminating circuit 6, and positions of incidence of gamma rays in the Y-direction are determined from the two added outputs.

Next, a specific construction of the light guide 20 will be described with reference to FIG. 6. FIG. 6 is a perspective view of the lattice frame of the light guide 20. The light guide 20 is formed mainly of a transparent material with a lattice frame 90 laid therein as shown in FIG. 6. The lattice frame 90 is formed by combining optical elements such as light reflecting elements or light transmitting elements (i.e. strips 91–95).

The light reflecting elements 11 and light transmitting elements 12 between the scintillators 1S, and the light reflecting elements 21 constituting the lattice frame 90 of the light guide 20, are formed of polyester film having a multilayer structure of silicon oxide and titanium oxide, polished aluminum, a thin substrate coated with titanium oxide or barium sulfate, a thin substrate covered by white tape, or a thin smooth substrate with aluminum formed thereon by vapor deposition. A similar material is used where light transmitting elements are substituted for the light reflecting elements 21 of the light guide 20.

Figure 7:
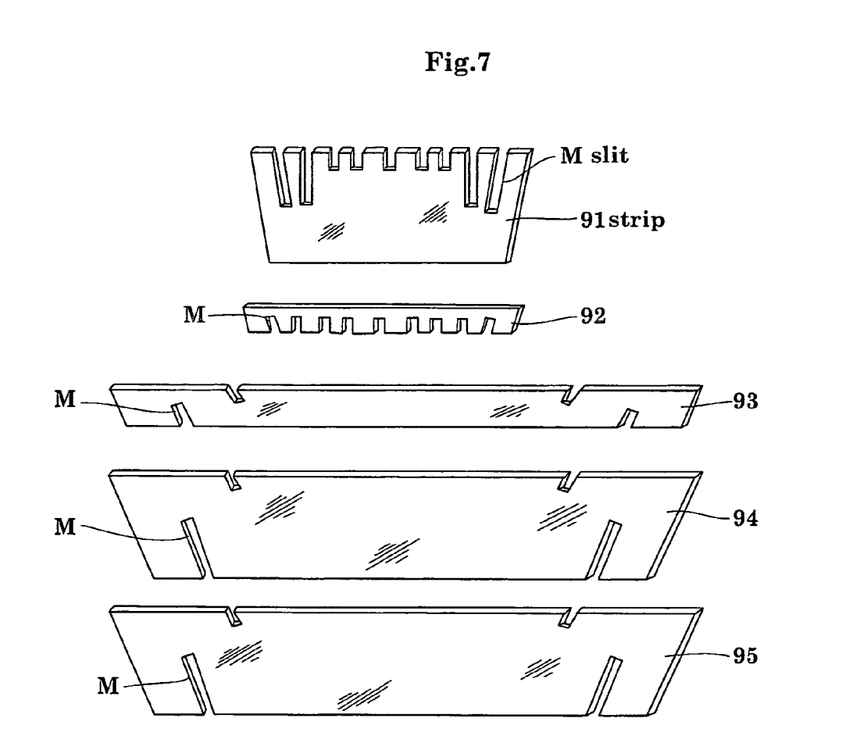
FIG. 7 is an exploded perspective view showing optical elements constituting the lattice frame.

Next, a method of manufacturing the light guide 20 will be described with reference to FIG. 7. FIG. 7 is an exploded perspective view showing the optical elements constituting the lattice frame. The optical elements comprise the above light reflecting elements or light transmitting elements, or a combination thereof. As shown in FIG. 7, the optical elements are in the form of thin strips 91–95 each defining slits M therein. The optical elements are combined by means of the slits M to form the lattice frame 90. The fabrication of the lattice frame 90 corresponds to step (A) in this invention.

The strips 91–95 may be contoured by dicing, laser cutting, cutting with a cutting tool, etching or punching. The strips 91–95, because they are thin, may be cut easily and precisely.

Figure 8:
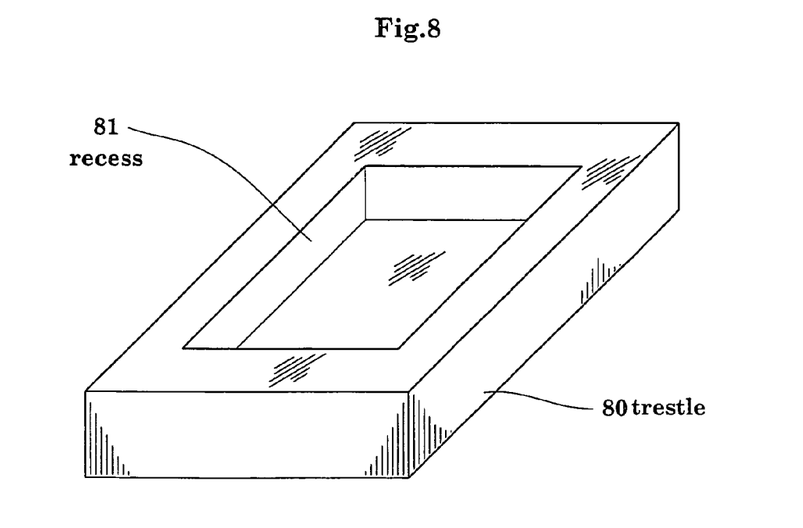
FIG. 8 is a perspective view of a trestle for use in manufacture of the radiation detector.

Next, a method of manufacturing the radiation detector using this light guide 20 will be described with reference to FIGS. 6 through 8. FIG. 8 is a perspective view of a trestle for use in manufacture of the radiation detector. In manufacture, as shown in FIG. 8, a rectangular trestle 80 is prepared, which has a recess 81 for receiving the lattice frame 90 therein. The lattice frame 90 shown in FIG. 6 is placed in the recess 81 of the trestle 80. The recess 81 has an area and depth for completely surrounding the lattice frame 90. A release agent is applied to inner surfaces of the recess 81 beforehand for allowing the light guide as a finished product (not shown) to be removed easily from the recess 81. The trestle 80 corresponds to the rectangular vessel in this invention.

A thoroughly defoamed, optically transparent liquid resin is poured into the recess 81 of the trestle 80. The liquid resin, preferably, is a transparent epoxy or acrylic resin. After the liquid resin cures, the lattice frame 90 and liquid resin are integrated as a cured resin object. The object is removed, and contoured by cutting and polishing to make the light guide 20 as shown in FIG. 3. The pouring of the liquid resin corresponds to step (B) in this invention. The process up to the contouring corresponds to step (C) in this invention.

By pouring in the defoamed liquid resin, the cured resin becomes free of voids which would lower resolution. A method of defoaming is not limited to the time of pouring in of the defoamed liquid resin. After placing the trestle 80 in a space (e.g. a chamber) that may be vacuum-degassed, the liquid resin may be poured in while carrying out vacuum degassing. In the above example, after the lattice frame 90 is placed in the recess 81 of the trestle 80, the liquid resin is poured in and is allowed to cure. Instead, after pouring in the liquid resin and before the resin cures, the lattice frame 90 may be placed in the recess 81 of the trestle 80.

The radiation detector RDA of high resolution may be realized simply by using the light guide 20 manufactured as described above. The above manufacturing method assures a high degree of shaping accuracy even where the scintillators 1S have a small sectional area, for example. A thickness and angles of the light reflecting elements 21 or light transmitting elements may be selected freely, and no gaps are formed between these elements and cured transparent resin, thereby assuring high reflecting efficiency. The optical elements such as the light reflecting elements 21 may easily be adjusted to an oblique angle. The optical elements may be arranged in the light guide 20 without cutting them with a dicing saw or wire saw, thereby realizing the radiation detector 20 with high finishing accuracy.

The position, length and angle of each light reflecting element 21 in the light guide 20 are adjusted so that the quantity of light incident on the photomultiplier tubes 301–304 varies equally according to the positions of the scintillators 1S on which gamma rays impinge. In this embodiment, the light reflecting elements 21 corresponding to the optical elements are (a) adjusted to predetermined intervals in the direction of arrangement of the scintillator array 10, (b) adjusted to predetermined angles relative to the direction of arrangement of the scintillator array 10, and (c) adjusted to have intervals different from the intervals between the scintillators 1S. More particularly, as shown in FIG. 9B, an example of adjustment (a) arranges the light reflecting elements 21 at unequal intervals, and an example of adjustment (b) sets the outermost light reflecting elements 21 inclined at an oblique angle relative to the direction of arrangement of the scintillator array 10. These adjustments made to the light reflecting elements 21 improve the discriminating ability to maintain high resolution and high image quality.

Where the radiation detector RDA of high resolution and high image quality is used in a diagnostic apparatus such as a PET apparatus or SPECT apparatus, images of high quality may be obtained from the apparatus also. Where, for example, a site of interest has a tumor, the tumor may be outputted on the images easily and accurately. The scintillators 1S arranged at intervals of 2.5 mm allow an accurate output of a tumor with a diameter of about 3.0 mm in the center of a visual field.

The light guide 20 has inclined outer peripheries so that the perimeter of the plane of the light guide 20 opposed to the photomultiplier tubes 301–304 matches the perimeter of the plane of the photomultiplying members 301a–304a opposed to the light guide 20, and that the perimeter of the plane of the scintillator array 10 opposed to the light guide 20 matches the perimeter of the plane of the light guide 20 opposed to the scintillator array 10. With this construction, the light from the scintillators 1S enters the light guide 20 without escaping outside the light guide 20, and the light from the light guide 20 enters the photomultiplying members 301a–304a without escaping outside the photomultiplying members 301a–304a.

The light reflecting elements 21 adjoining the outer peripheries of the light guide 20, i.e. the outermost reflecting elements 21, are set at an oblique angle to the direction of arrangement of the scintillator array 10 also for the reason of avoiding the light being trapped in narrow spaces between the outer peripheries and the next reflecting elements 21. That is, light can smoothly enter the photomultiplier tubes 301–304 since the outermost reflecting elements 21 are inclined to maintain unrestricted spaces inwardly of the inclined outer peripheries.

This invention is not limited to the above embodiment, but may be modified as follows:

(1) In the foregoing embodiment, the radiation detector is constructed for detecting gamma rays. The invention is applicable also to a detector for detecting radiation other than gamma rays, e.g. X rays.

(2) In the foregoing embodiment, all three adjustments of the reflecting elements 21 are used in combination, which are (a) adjustment to predetermined intervals in the direction of arrangement of the scintillator array 10, (b) adjustment to predetermined angles relative to the direction of arrangement of the scintillator array 10, and (c) adjustment to have intervals different from the intervals between the scintillators 1S. As long as the quantity of light incident on the photomultiplier tubes 301–304 varies equally according to the positions of the scintillators 1S on which gamma rays impinge, only one of adjustments (a) to (c) may be used, or adjustments (a) and (b), (b) and (c) or (c) and (a) may be combined. That is, at least one of adjustments (a) to (c) may be used for the light guide 20.

(3) In the foregoing embodiment, the light reflecting elements 21 are used as the optical elements forming the light guide 20. Light transmitting elements may be used in place of the light reflecting elements, or light reflecting elements and light transmitting elements may be used in combination.

(4) In the foregoing embodiment, the liquid resin is poured in after a release agent is applied to facilitate removal of the light guide as a finished product from the trestle 80. It is not absolutely necessary to apply the release agent.

(5) In the foregoing embodiment, the liquid resin is defoamed when poured, but it is not necessary to defoam the liquid resin.

(6) In the foregoing embodiment, the light reflecting elements 21 inclined at an angle to the direction of arrangement of the scintillator array 10 are the light reflecting elements 21 next to the outer peripheries of the light guide 20. Other light reflecting elements 21 may also be adjusted to an oblique angle as necessary. The remaining light reflecting elements 21 may be set to a predetermined angle, e.g. perpendicular, to the direction of arrangement of the scintillator array 10. The same applies to light transmitting elements.

(7) In the foregoing embodiment, the outer peripheries of the light guide 20 are inclined so that the perimeter of the plane of the light guide 20 opposed to the photomultiplier tubes 301–304 matches the perimeter of the plane of the photomultiplying members 301a–304a opposed to the light guide 20, and that the perimeter of the plane of the scintillator array 10 opposed to the light guide 20 matches the perimeter of the plane of the light guide 20 opposed to the scintillator array 10. A construction may be employed in which the perimeter of the plane of the light guide 20 opposed to the photomultiplier tubes 301–304 matches the perimeter of the plane of the photomultiplying members 301a–304a opposed to the light guide 20, or in which the perimeter of the plane of the scintillator array 10 opposed to the light guide 20 matches the perimeter of the plane of the light guide 20 opposed to the scintillator array 10.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiation detector having a scintillator array formed of a plurality of scintillators in a compact, two-dimensional arrangement, a light guide optically combined to said scintillator array, and a plurality of photomultiplier tubes smaller in number than said scintillators and optically combined to said light guide, wherein:

said light guide is formed of at least a lattice frame having plate-like optical elements combined crosswise, and a transparent resin, said lattice frame defining a plurality of cubicles; and said optical elements forming the cubicles are subjected to at least one of (a) an adjustment to predetermined intervals in a direction of arrangement of said scintillator array, (b) an adjustment to a predetermined angle to the direction of arrangement of said scintillator array, and (c) an adjustment to intervals different from intervals between said scintillators.

2. A radiation detector as defined in claim 1, wherein (a) said adjustment to predetermined intervals in a direction of arrangement of said scintillator array is made to arrange said optical elements at uneven intervals.

3. A radiation detector as defined in claim 1, wherein (b) said adjustment to a predetermined angle to the direction of arrangement of said scintillator array is made to incline said optical elements at an oblique angle to the direction of arrangement of said scintillator array.

4. A radiation detector as defined in claim 1, wherein said light guide is constructed such that a perimeter of a plane of said scintillator array opposed to said light guide matches a perimeter of a plane of said light guide opposed to said scintillator array.

5. A radiation detector as defined in claim 1, wherein each of said photomultiplier tubes includes a vacuum tube, and a photomultiplying member contained in said vacuum tube, said light guide being constructed such that a perimeter of a plane of said light guide opposed to said photomultiplier tubes matches a perimeter of a plane of the photomultiplying members opposed to said light guide.

6. A radiation detector as defined in claim 1, wherein each of said photomultiplier tubes includes a vacuum tube, and a photomultiplying member contained in said vacuum tube, said light guide having outer peripheries thereof inclined such that such that a perimeter of a plane of said scintillator array opposed to said light guide matches a perimeter of a plane of said light guide opposed to said scintillator array, and that a perimeter of a plane of said light guide opposed to said photomultiplier tubes matches a perimeter of a plane of the photomultiplying members opposed to said light guide.

7. A radiation detector as defined in claim 6, wherein those of said optical elements adjoining said outer peripheries are inclined to match inclinations of said outer peripheries.

8. A radiation detector as defined in claim 1, wherein said optical elements comprise light reflecting elements or light transmitting elements.

9. A method of manufacturing a radiation detector having a scintillator array formed of a plurality of scintillators in a compact, two-dimensional arrangement, a light guide optically combined to said scintillator array, and a plurality of photomultiplier tubes smaller in number than said scintillators and optically combined to said light guide, said method comprising:

(A) a step of fabricating a lattice frame by combining a plurality of plate-like optical elements crosswise;

(B) a step of pouring a transparent liquid resin into a rectangular vessel for receiving said lattice frame, before or after placing said lattice frame in said rectangular vessel; and (C) a step of removing from said rectangular vessel a cured resin object integrating said liquid resin having cured and said lattice frame, and contouring the resin object to make said light guide;

wherein the step (A) above is executed to combine said optical elements by making at least one of (a) an adjustment to predetermined intervals in a direction of arrangement of said scintillator array, (b) an adjustment to a predetermined angle to the direction of arrangement of said scintillator array, and (c) an adjustment to intervals different from intervals between said scintillators.

10. A method of manufacturing a radiation detector as defined in claim 9, wherein (a) said adjustment to predetermined intervals in a direction of arrangement of said scintillator array is made to arrange said optical elements at uneven intervals.

11. A method of manufacturing a radiation detector as defined in claim 9, wherein (b) said adjustment to a predetermined angle to the direction of arrangement of said scintillator array is made to incline said optical elements at an oblique angle to the direction of arrangement of said scintillator array.

12. A method of manufacturing a radiation detector as defined in claim 9, wherein said light guide is constructed such that a perimeter of a plane of said scintillator array opposed to said light guide matches a perimeter of a plane of said light guide opposed to said scintillator array.

13. A method of manufacturing a radiation detector as defined in claim 9, wherein each of said photomultiplier tubes includes a vacuum tube, and a photomultiplying member contained in said vacuum tube, said light guide being constructed such that a perimeter of a plane of said light guide opposed to said photomultiplier tubes matches a perimeter of a plane of the photomultiplying members opposed to said light guide.

14. A method of manufacturing a radiation detector as defined in claim 9, wherein each of said photomultiplier tubes includes a vacuum tube, and a photomultiplying member contained in said vacuum tube, said light guide having outer peripheries thereof inclined such that such that a perimeter of a plane of said scintillator array opposed to said light guide matches a perimeter of a plane of said light guide opposed to said scintillator array, and that a perimeter of a plane of said light guide opposed to said photomultiplier tubes matches a perimeter of a plane of the photomultiplying members opposed to said light guide.

15. A method of manufacturing a radiation detector as defined in claim 14, wherein those of said optical elements adjoining said outer peripheries are inclined to match inclinations of said outer peripheries.

16. A method of manufacturing a radiation detector as defined in claim 9, wherein said optical elements comprise light reflecting elements or light transmitting elements.

17. A method of manufacturing a radiation detector as defined in claim 9, wherein said liquid resin is an optically transparent epoxy resin.

18. A method of manufacturing a radiation detector as defined in claim 9, wherein said liquid resin is an optically transparent acrylic resin.

19. A method of manufacturing a radiation detector as defined in claim 9, wherein a release agent is applied to said rectangular vessel before executing said step (B) of pouring the transparent liquid resin into the rectangular vessel.

20. A method of manufacturing a radiation detector as defined in claim 9, wherein said liquid resin is defoamed when executing said step (B) of pouring the transparent liquid resin into the rectangular vessel.

* * * * *